(12) United States Patent
Nakamura

(10) Patent No.: US 10,675,099 B2
(45) Date of Patent: Jun. 9, 2020

(54) NEEDLE INSERTION GUIDE DEVICE AND SYSTEM, AND METHOD OF PROVIDING CONTROL GUIDANCE FOR NEEDLE INSERTION GUIDE DEVICE

(71) Applicant: Canon USA Inc., Melville, NY (US)

(72) Inventor: Hitoshi Nakamura, Boston, MA (US)

(73) Assignee: Canon U.S.A., Inc., Melville, NY (US)

( * ) Notice: Subject to any disclaimer, the term of this patent is extended or adjusted under 35 U.S.C. 154(b) by 285 days.

(21) Appl. No.: 15/713,327

(22) Filed: Sep. 22, 2017

(65) Prior Publication Data

US 2019/0090953 A1 Mar. 28, 2019

(51) Int. Cl.
*A61B 34/20* (2016.01)
*G09B 5/02* (2006.01)
(Continued)

(52) U.S. Cl.
CPC .......... *A61B 34/20* (2016.02); *A61B 17/3211* (2013.01); *A61B 17/3403* (2013.01);
(Continued)

(58) Field of Classification Search
CPC ....... A61B 90/11; A61B 90/39; A61B 90/067; A61B 90/94; A61B 17/3403;
(Continued)

(56) References Cited

U.S. PATENT DOCUMENTS

| | | |
|---|---|---|
| 5,196,019 A | 3/1993 | Davis et al. |
| 5,957,934 A | 9/1999 | Rapoport |

(Continued)

FOREIGN PATENT DOCUMENTS

| | | |
|---|---|---|
| JP | 2015-047303 A | 3/2015 |
| WO | 2010/096149 A1 | 8/2010 |
| WO | 2015041516 A1 | 3/2015 |

OTHER PUBLICATIONS

Joshua Morse; Development of a needle insertion end effector for robot assistance of ultrasound-guided regional anesthesia; Aug. 2014; pp. 1-131; McGill University; Montreal, Quebec, Canada.
(Continued)

*Primary Examiner* — Ryan J. Severson
*Assistant Examiner* — Mohamed G Gabr
(74) *Attorney, Agent, or Firm* — Canon U.S.A., Inc. IP Division

(57) ABSTRACT

A medical tool insertion guide device includes a base portion composed primarily of electromagnetically transmissive material but has a first component composed of electromagnetically absorptive material. The device also includes a movable portion composed primarily of the electromagnetically transmissive material, but has a second component composed of absorptive material. The movable portion is mounted, but movable by rotation or translation relative, to the base portion. An encoder sensor is mounted to one portion, and an encoder scale is mounted to the other, and the sensor faces the scale when mounted. The components can include fiducial markers. The transmissivity and absorptivity can be in a particular band(s), such as an X-ray band. The medical tool can be a needle, a medical probe, a scalpel, etc. A computer based method of providing control guidance for the device is provided, and a program therefor can be stored in a storage medium.

32 Claims, 14 Drawing Sheets

(51) Int. Cl.
*A61B 17/3211* (2006.01)
*A61B 17/34* (2006.01)
*A61B 90/11* (2016.01)
*A61B 90/00* (2016.01)
*A61B 17/00* (2006.01)
*G09B 23/28* (2006.01)

(52) U.S. Cl.
CPC ............... *A61B 90/11* (2016.02); *G09B 5/02* (2013.01); *G09B 23/28* (2013.01); *G09B 23/285* (2013.01); *A61B 2017/00119* (2013.01); *A61B 2017/3407* (2013.01); *A61B 2034/2051* (2016.02); *A61B 2034/2055* (2016.02); *A61B 2034/2059* (2016.02); *A61B 2090/067* (2016.02); *A61B 2090/3762* (2016.02); *A61B 2090/3937* (2016.02); *A61B 2090/3954* (2016.02); *A61B 2090/3966* (2016.02); *A61B 2090/3983* (2016.02); *A61B 2560/063* (2013.01)

(58) Field of Classification Search
CPC .... A61B 2017/3407; A61B 2017/3409; A61B 2017/00911; A61B 2090/374; A61B 2090/3954; A61B 2090/3762; A61B 2090/3966; A61B 2090/3983; A61B 2090/067; A61B 2090/0807; A61B 2090/0811; A61B 2090/363; A61B 2090/376; A61B 2090/3937; A61B 10/023; A61B 34/20; A61B 2034/107; A61B 2034/2048; A61B 2034/2051; A61B 2034/2055; A61B 2034/2059; A61B 2560/063
See application file for complete search history.

(56) References Cited

U.S. PATENT DOCUMENTS

| | | | |
|---|---|---|---|
| 6,119,032 | A | 9/2000 | Martin et al. |
| 6,185,445 | B1 | 2/2001 | Knuttel |
| 6,487,431 | B1 | 11/2002 | Iwano et al. |
| 6,505,065 | B1 | 1/2003 | Yanof et al. |
| 7,014,361 | B1 | 3/2006 | Ein-Gal |
| 7,083,608 | B2 | 8/2006 | Tomita et al. |
| 7,187,104 | B2 | 3/2007 | Yamamoto et al. |
| 7,824,417 | B2 | 11/2010 | Magnusson et al. |
| 8,308,740 | B2 | 11/2012 | Tolley et al. |
| 8,511,316 | B2 | 8/2013 | Boese et al. |
| 9,125,676 | B2 | 9/2015 | Sahni |
| 9,222,996 | B2 | 12/2015 | Fujimoto et al. |
| 9,254,177 | B2 | 2/2016 | Stratton et al. |
| 9,408,627 | B2 | 8/2016 | Sahni |
| 9,433,390 | B2 | 9/2016 | Nathaniel et al. |
| 9,471,894 | B2 | 10/2016 | Palamarchuk et al. |
| 9,554,779 | B2 | 1/2017 | Larson et al. |
| 2004/0260312 | A1 | 12/2004 | Magnusson et al. |
| 2006/0229641 | A1 | 10/2006 | Gupta et al. |
| 2009/0143672 | A1 | 6/2009 | Harms et al. |
| 2010/0063496 | A1 | 3/2010 | Trovato et al. |
| 2010/0082040 | A1 | 4/2010 | Sahni |
| 2011/0190787 | A1 | 8/2011 | Sahni |
| 2011/0202308 | A1 | 8/2011 | Kishida et al. |
| 2012/0022368 | A1 | 1/2012 | Brabrand et al. |
| 2012/0065496 | A1 | 3/2012 | Stratton et al. |
| 2014/0022245 | A1 | 1/2014 | Brannan et al. |
| 2014/0107569 | A1 | 4/2014 | Fischer et al. |
| 2016/0038247 | A1 | 2/2016 | Bharadwaj et al. |
| 2016/0074063 | A1 | 3/2016 | Arimitsu et al. |
| 2017/0014200 | A1 | 1/2017 | Onuma et al. |
| 2017/0020557 | A1* | 1/2017 | Onuma .................. A61B 90/11 |

OTHER PUBLICATIONS

I. D. Coope, Circle fitting by linear and nonlinear least squares, Department of Mathematics, University of Canterbury, Christchurch, New Zealand, Revised May 1992, pp. Title page and 1-7, No. 69, and Accepted for publication in Journal of Optimization Theory and Applications, Feb. 1993, pp. 381-388, vol. 76, Issue 2.

* cited by examiner

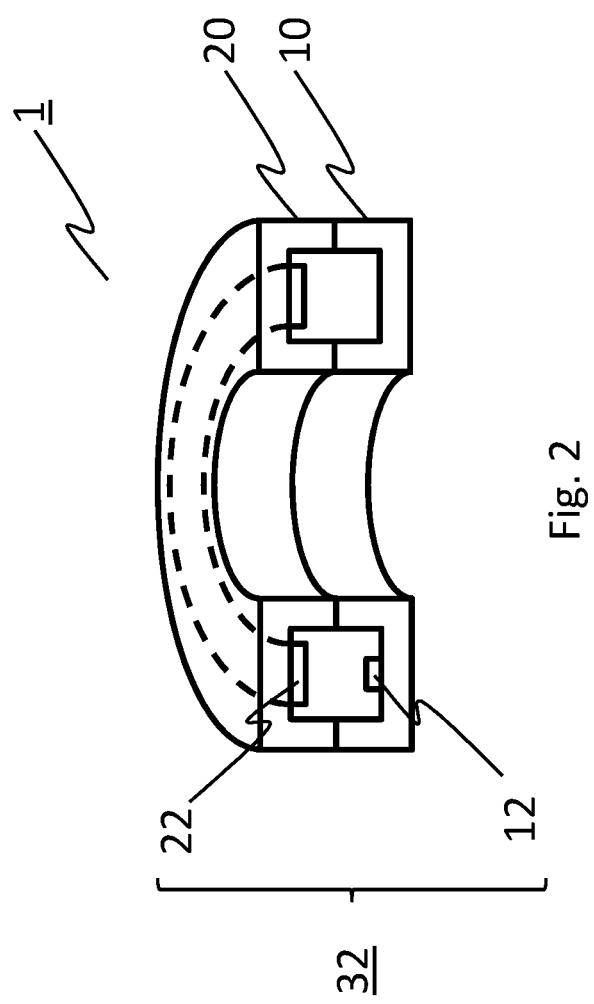

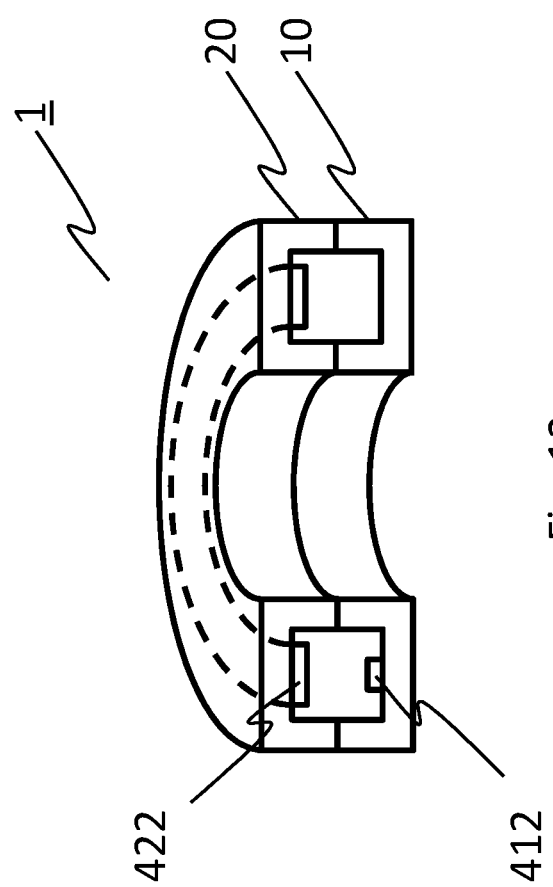

NEEDLE INSERTION GUIDE DEVICE AND SYSTEM, AND METHOD OF PROVIDING CONTROL GUIDANCE FOR NEEDLE INSERTION GUIDE DEVICE

BACKGROUND OF THE INVENTION

Field of the Invention

The present invention relates to a device for guiding insertion of a medical tool, such as a needle, a scalpel, or a medical probe, into a patient, and to a method of providing control guidance for such device.

Description of the Related Art

United States Patent Application Publication No. 2016-0074063 discusses a positioning apparatus including a needle holder having a through hole for regulating needle placement and movement, a needle positioning unit, and an engagement member that fixes a position of the needle holder with respect to the needle positioning unit. The needle holder is either at least partially detachably attached to the needle positioning unit or deformable. The positioning apparatus may be designed to accommodate the placement of multiple needles.

PCT Patent Application Publication WO2015041516 discusses a system for aligning a medical device with respect to a location on a patient with an insertion axis extending through the location and a predetermined target location in the patient. The system comprises (1) a base arranged for connecting the system to the surroundings, for instance a patient support of a scanner, (2) an alignment device comprising a stationary part and a axial guide, wherein the axial guide is arranged for guiding the medical device along a guiding axis, wherein the alignment device is arranged for rotating the axial guide about a remote center of rotation while the location of the remote center of rotation is fixed with respect to the stationary part and while the guiding axis extends through the remote center of rotation, and (3) an arm connecting the base and the stationary part of the alignment device.

United States Patent Application Publication No. 2009-0143672 discusses that NMR/MRI imaging, a location is noted for a point in the imaged space, and referred to a reference location so that the point in imaged space is known thereafter, without the need to locate the point again in further imaging steps. For breast cancer diagnosis and biopsy, a breast holding fixture immobilizes the breast. A volumetric image is taken encompassing a portion of the breast. In the same or a subsequent image, a fiducial mark is detected to determine the position of a holder for a biopsy tool or other modality. The tissue feature can be a tumor, cyst or tubal lesion, made temporarily visible in the image by perfusion with a contrast agent. After the contrast agent dissipates, the location of the tissue feature may still be determined by reference to the position of the fiducial marker, which is optionally adjustable by post-imaging metered displacement.

United States Patent Application Publication No. 2012-0065496 discusses an apparatus for imaging a body part of a subject, for example using MRI. The apparatus includes a housing for at least partially surrounding a body part, such as a head, and a first fiducial marker assembly retained at least partially within the housing that includes one or more fiducial markers and a datum feature. The position of the datum feature is fixed relative to the one or more fiducial markers. The first fiducial marker assembly is moveable with respect to the housing and the datum feature is accessible from outside of the housing.

SUMMARY OF THE INVENTION

According to an aspect of the present invention, a medical tool insertion guide device includes a base portion and a movable portion. The base portion is composed primarily of material transmissive of at least one band of electromagnetic radiation, but has a first component composed of material absorptive of the at least one band of electromagnetic radiation. The base portion has a first mounting surface. The movable portion is composed primarily of material transmissive of the at least one band of electromagnetic radiation, but has a second component composed of material absorptive of the at least one band of electromagnetic radiation. The movable portion is configured to be mounted to the base portion and when so mounted movable relative to the base portion. The movable portion has a second mounting surface that faces the first mounting surface of the base portion when the movable portion is mounted to the base portion. The medical tool insertion guide device includes an encoder having an encoder sensor and an encoder scale. One of the encoder sensor and the encoder scale is mounted to the first mounting surface, and the other of the encoder sensor and the encoder scale is mounted to the second mounting surface. The encoder sensor faces the encoder scale when the movable portion is mounted to the base portion. The first component and the second component can include, for example, one or more fiducial marker. Moreover, the at least one band of electromagnetic radiation can include an X-ray band, for example, to support usage of medical X-ray CT scans. Moreover, the movable portion can be mounted to the base portion either by a rotatable mounting, a mounting that supports linear motion, a mounting that supports motion along an arc, or more than one of the above. The medical tool can be, for example, a needle, a medical probe, or a scalpel.

According to another aspect of the present invention, a method is disclosed of providing control guidance for a medical tool insertion guide device using at least one scan of the medical tool insertion guide device by an electromagnetic radiation scan apparatus, the medical tool insertion guide device having an encoder that provides a first measure of an alignment provided to a medical tool by the medical tool insertion guide device, the medical tool insertion guide device having at least one fiducial marker from which a second measure of the alignment provided to the medical tool by the medical tool insertion guide device is provided by computer processing of the at least one scan of the medical tool. The method includes comparing the first measure to the second measure by determining a difference between a value of the first measure and a value of the second measure, determining whether the difference between the value of the first measure and the value of the second measure exceeds a predetermined threshold, and providing a warning to an operator of the medical tool insertion guide device that first measure may be inaccurate in response to the difference between the value of the first measure and the value of the second measure exceeding the predetermined threshold.

According to another aspect of the present invention, the method may additionally or alternatively include calculating a first error magnitude estimate of the first measure based on at least one of a position error of the encoder and an amount of slack between portions of the medical tool insertion guide device, calculating a second error magnitude estimate of the second measure based on at least a quantization error component of resolution error of the at least one scan of the medical tool insertion guide device by an electromagnetic radiation scan apparatus, comparing the first error magnitude to the second error magnitude, and advising the operator, based on a result of the comparing, regarding which of the first measure and the second measure is more accurate.

Moreover, according to another aspect of the present invention, a non-transitory computer-readable medium stores a program of instructions that when executed by a computer cause the computer to perform such methods.

Further features and aspects of the present invention will become apparent from the following description of example embodiments with reference to the attached drawings.

BRIEF DESCRIPTION OF THE DRAWINGS

FIG. 2 is a sectional view of the needle insertion guide device according to the first example embodiment.

FIG. 12 is a sectional view of the needle insertion guide device that includes a magnetic encoder according to another example embodiment.

DESCRIPTION OF THE EMBODIMENTS

Various example embodiments, features, and aspects of the present invention are described in detail below with reference to the drawings. According to an aspect of the present invention, a device for guiding insertion of a medical tool is provided that is capable of providing more than one means for guiding at least one of the angle and depth of insertion of the medical tool into the patient. In accordance with another aspect of the present invention, the medical tool can be a needle, a medical probe, or a scalpel. A method of providing medical operator (e.g., physician, nurse, medical technician, or other medical care provider) with guidance instructions to secure at least one of a desired insertion angle and a desired insertion depth area is also provided. In many of the examples discussed below, the medical tool is presumed to be a needle. Nonetheless, the needle insertion guide device 1 can also be used to guide other medical tools, such as a medical probe and/or a scalpel. If the needle insertion needle insertion guide device 1 includes a needle holder (discussed below), then the needle holder can be shaped to accommodate needles, medical probes, and/or scalpels, for example, as discussed below.

Figure 1:
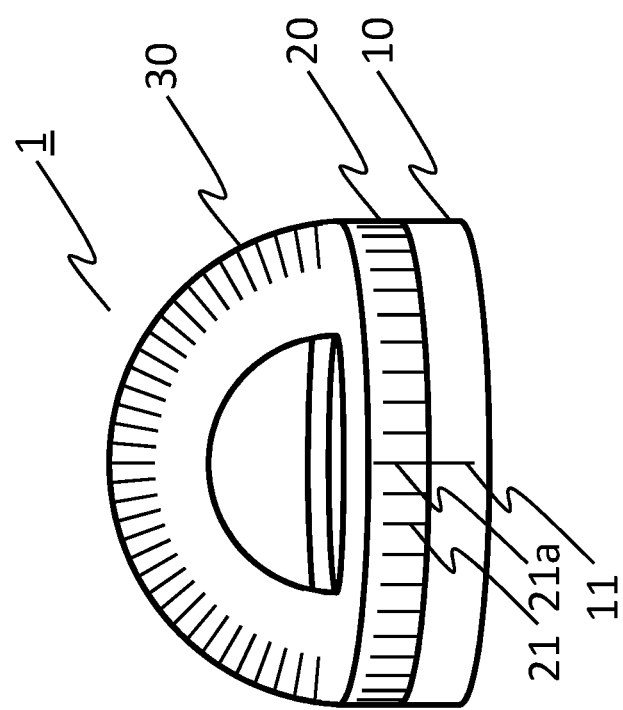
FIG. 1 is a perspective view of a needle insertion guide device according to a first example embodiment.

Referring now to FIG. 1, FIG. 2, and FIGS. 3A-3E, there is shown a needle insertion guide device 1 according to a first example embodiment. FIG. 1 is a perspective view, FIG. 2 is a sectional view, and FIGS. 3A-3E are top views. The needle insertion guide device 1 comprises a fixed part 10 and a rotatable part 20. Both the fixed part 10 and the rotatable part 20 are ring shaped. A handle 30 is attached to, or formed into, the rotatable part 20. The handle 30 can, for example, be arc shaped, with two ends of the arc shaped handle 30 being attached to, or formed into, the opposite sides of the ring shape of the rotatable part 20, which beneficially provides both support against deformation of the ring shape of the rotatable part 20 and also easy access to the interior of the ring shape of the rotatable part 20 through which a needle can be inserted.

The fixed part 10 has an index line 11, and the rotatable part 20 has a plurality of index lines 21. The fixed part 10, the rotatable part 20, and the handle 30 are each composed primarily of material that is transmissive of at least one band of electromagnetic radiation. In this embodiment, the relevant bands are those used for medical X-ray CT scanning, and the material is a moldable material that is transmissive to such X-rays, such as a moldable plastic. For example, the fixed part 10, the rotatable part 20, and the handle 30 can be formed by injection molding a thermoplastic or thermosetting polymer having high transmittance at the scanning frequency. Accordingly, if applied to a patient undergoing a medical X-ray CT scan, most of the needle insertion guide device 1 is either not seen in the resulting X-ray CT scan image(s), or alternatively merely shades a portion of the resulting scan image(s) without obscuring the medical details shown in the resulting scan image(s).

An operator (e.g., physician, nurse, medical technician, or other medical care provider) can determine a relative rotation angle between the fixed part 10 and the rotatable part 20 using the index lines 11 and 21. One of the index lines 21a of the plurality of index lines 21 is marked, for example by color, shape, width, or length, as a centering one of the lines 21. Accordingly, when the index line 21a and the index 11 are aligned (i.e. lie on the same ray extending from the axis of rotation (marked O in FIGS. 3A-3E) of the rotatable part 20), the relative rotation angle between the fixed part 10 and the rotatable part 20 is considered to be 0 degrees. The handle 30 also has a plurality of index lines 31. The user can read an insertion angle on the handle 30 using the index lines 31. The rotatable part 20 is rotably mounted to the fixed part 10. The rotatable part 20 can thus rotate relative to the fixed part 10 on the rotable mounting. The rotatable part 20 can be removed from the fixed part 10, for example, to allow the operator or a medical care provider greater access to the patient or to facilitate cleaning of the needle insertion guide device 1. The removal can be performed by the operator by hand, that is, without need to use tools to remove the movable part 20 from the fixed part 10. Likewise, the movable part 20 can be mounted to the fixed part 10 by hand, without the need to use tools fasten the movable part 20 to the fixed part 10. Both the fixed part 10 and rotatable part 20 have a respective channel. The channel of the rotatable part 20 is disposed to face the channel of the fixed part 10. In this embodiment, the rotatable part 20 and fixed part 10 meet at a contact plane, and the channel of the rotatable part 20 faces the channel of the fixed part 10 across the contact plane. Points of contact of the rotatable part 20 and the fixed part 10 need not be in the aforementioned contact plane.

An encoder 32 comprising an encoder sensor 12 and an encoder scale 22 are included in the needle insertion guide device 1. In this embodiment, the encoder 32 is an optical encoder. The encoder sensor 12 and a fiducial marker 13 are disposed in the channel of fixed part 10. The encoder scale 22 and a plurality of fiducial markers 23, 24, and 25 are disposed in the channel of rotatable part 20. The fiducial markers 13, 23, 24, and 25 are composed of material that is absorptive of at least a portion of the at least one band of electromagnetic radiation. In this embodiment, the fiducial markers 13, 23, 24, and 25 are absorptive of X-rays used for medical X-ray CT scanning. Accordingly, if the needle insertion guide device 1 is applied to a patient and the patient then undergoes a medical X-ray CT scan, the fiducial markers 13, 23, 24, and 25 may be seen in the resulting X-ray CT scan image(s). In this embodiment, the encoder scale 22 is mounted to the bottom of the channel of the rotatable part 20. Mounting the encoder sensor 12 in a channel shields the encoder sensor 12 from adverse environmental conditions, such as ambient radiation and/or medical debris. Mounting the encoder scale 22 in a channel similarly shields the encoder scale 22 from such adverse environmental conditions. Alternatively, the encoder scale 22 can be printed on or embedded into the bottom of the channel of the rotatable part 20. In this embodiment, the encoder scale 22 is ring shaped. Alternatively, the encoder scale 22 can be arc shaped rather than ring shaped. The encoder sensor 12 and the encoder scale 22 are opposed to one another so that the encoder sensor 12 faces the encoder scale 22.

The encoder sensor 12 reads the encoder scale 22 and outputs first angle information that indicates a measure of a relative rotation angle between the encoder sensor 12 and the encoder scale 22. The first angle information provides an estimate of the direction angle of the handle 30 of the rotatable part 20 in the top views of FIGS. 3A-3E. In this embodiment, the encoder 32 is an absolute encoder which provides the measure of the relative rotation angle either in degrees or radians. Alternatively, a relative encoder can be used, for example, that provides an output signal that indicates the number of index lines 21 of the rotatable part 20 that are shifted over a given point when the rotatable part 20 is rotated along with the angular direction in which index lines 21 are shifted, and the first angle information can be calculated based on the output signal of the relative encoder.

In this embodiment, the fiducial marker 13 is placed behind index line 11 and is considered to be a 0 degrees position of the encoder 32. The fiducial markers 23, 24, and 25 are disposed at 270 degrees, 0 degrees, and 90 degrees angle positions of the encoder scale 22 respectively. When the relative rotation angle between the fixed part 20 and the rotatable part 20 is 0 degrees, as determined by the index line 21a being in alignment with the index 11, the relative rotation angle between the encoder sensor 12 and the encoder scale 22 is likewise 0 degrees. However, when the encoder sensor 12 reads the encoder scale 22 and the first angle information output by the encoder sensor 12 may indicate that the measure of the relative rotation angle between the encoder sensor 12 and the encoder scale 22 differs from 0 degrees, for example, due to tolerances of the encoder sensor 12 and/or malfunction of the encoder 32. Ideally, when the relative rotation angle between the encoder sensor 12 and the encoder scale 22 is considered to have a value of 0 degrees, the fiducial marker 24 and the fiducial marker 13 are both centered on the same radial ray extending from the axis of rotation of the rotatable part 20.

In this embodiment, the fiducial markers 13, 23, 24, and 25 are equidistant from the rotational center of the rotatable part 20, and fiducial markers 23, 24, and 25 lie at apexes of an isosceles right triangle, and the center of the hypotenuse of the isosceles right triangle lies at the rotational center of the rotatable part 20. That is, the center of the triangle side between fiducial markers 23 and 25 lies at the rotational center of the rotatable part 20. Accordingly, in this embodiment, when the relative rotation angle between the encoder sensor 12 and the encoder scale 22 is 0 degrees, the fiducial markers 13 and 24 will appear to overlap one another or to be coextensive in a CT scan taken from a top view of image of the needle insertion guide device 1.

FIGS. 3A-3E show top views of the needle insertion guide device 1 including fiducial markers 13, 23, 24, and 25. The distance L from the rotational center of the rotatable part 20 to each of the fiducial markers 13, 23, 24, and 25 is the same. Accordingly, depending on the rotational angle of the rotatable part 20, the fiducial marker 13 can overlap any one of the other fiducial markers 23, 24, and 25 in the top views of FIGS. 3A-3E. Since the encoder scale 22 and fiducial markers 23, 24, and 25 rotate together, the first angle information ideally equals the relative angle between fiducial marker 13 and fiducial 24. In addition, the fiducial markers 13, 23, 24, and 25 absorb radiation, and are visible in CT scanned images.

Figure 4:
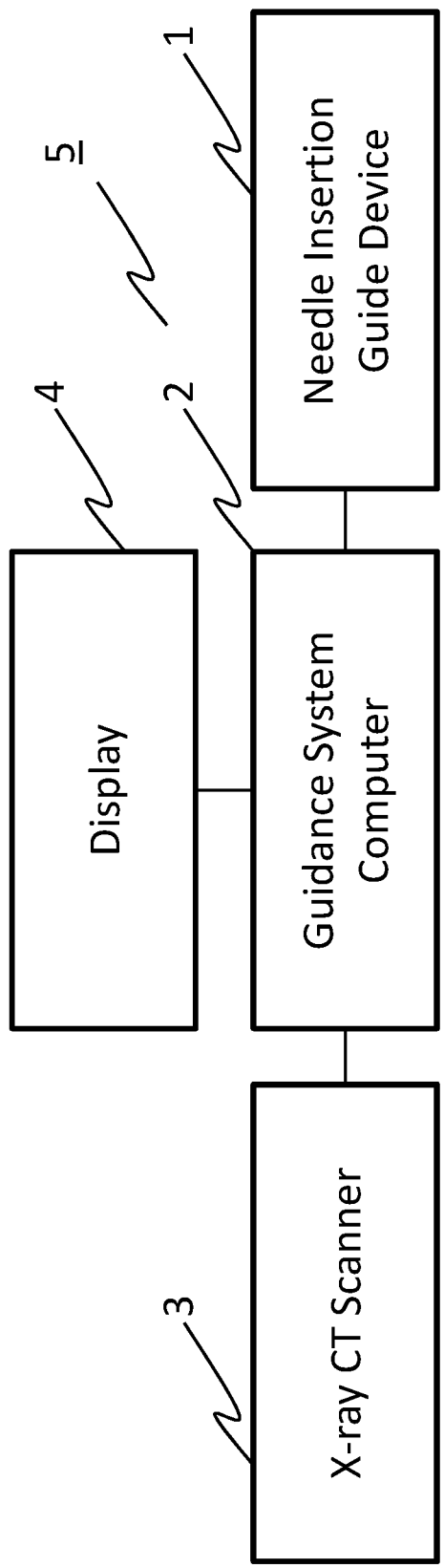
FIG. 4 is a block diagram of an image processing and guidance system according to the first example embodiment.

Referring now also to FIG. 4, there is shown a block diagram of an image processing and guidance system 5 according to the first example embodiment. The image processing and guidance system 5 includes the needle insertion guide device 1, a guidance system computer 2, an X-ray CT scanner 3, and a display 4. In this embodiment, the X-ray CT scanner 3 can be a conventional digital X-ray CT scanner configured to scan an object (such as a patient) and output a digital X-ray CT scan image signal of the object. In this embodiment, the guidance system computer 2 is a computer workstation programmed to perform image processing on X-ray CT scan output provided by the X-ray CT scanner 3. In particular, the guidance system computer 2 includes CPU and a memory, with the memory storing software for analyzing and displaying digital X-ray CT scan image signals. In this embodiment, the display 4 is a conventional computer display device. The image processing and guidance system 5 is interconnected in a star configuration, with the guidance system computer 2 serving as a hub of the image processing and guidance system 5, and the needle insertion guide device 1, the X-ray CT scanner 3, and with the display 4 each connected to the guidance system computer 2 by a distinct interconnection line.

The needle insertion guide device 1 and the image processing and guidance system 5 can be used for precise insertion and/or movement of a needle in a patient, for example, for targeted injection of drugs in a patient or to ablate tumors in an organ of the patient. The fixed part 10 of the needle insertion guide device 1 is affixed to the patient, for example, using medical tape. The needle insertion guide device 1 is used to adjust the angle of needle insertion. Because the operator inserts the needle by aligning with the needle insertion guide device 1, the operator can notice if the insertion angle is incorrect. Furthermore, the guidance system computer 2 detects any movement between the body of the patient and the needle insertion guide device 1, for example rotation of the rotatable part 20, and calculates the insertion angle currently provided by the needle insertion guide device 1. The insertion angle can be calculated using scanned images of the patient to whom the needle insertion guide device 1 is affixed. The X-ray CT scanner 3 scans the body of the patient to detect targets for treatment. The X-ray CT scanner 3 can include a bed which a patient lies down and which moves during scanning operations. The X-ray CT scanner 3 scans multiple slices of two dimensional information on different planes and reconstructs three dimensional images from the multiple slices of two dimensional information. The display 4 shows the guidance of the guidance system computer 2. In addition, the guidance system computer 2 reads angle information which the encoder 32 outputs from the needle insertion guide device 1, reads images from X-ray CT scanner 3, and shows information on display 4 that informs the operator of the insertion angle to use and the insertion depth to which to insert the needle to reach a target location. A target location for the needle to reach can specified, for example, either by the operator on the displayed X-ray CT scan or by the guidance system based on analysis of the output of the X-ray CT scanner 3. Once the operator reads the insertion angle and the insertion depth on the display 4, the operator rotates the rotatable part 20 to the insertion angle and then inserts the needle to the insertion depth indicated on the display 4. Additional scans by the X-ray CT can be taken so that the operator can verify whether the needle has reached the target location.

The image processing and guidance system 5 indicates to the operator when the rotatable part 20 is at the proper angle using either one of two operations. First, the first angle information output by the encoder sensor 12 of the encoder 32 can be displayed on the display 4, and the operator can rotate the rotatable part 20 until the appropriate angle is provided. Second, the operator can alternatively use second angle information determined by performing image processing on the output of the X-ray CT scanner 3 as discussed below. Furthermore, the guidance system computer 2 can also indicate to the operator on the display 4 which of the two operations is more accurate, or can simply display a most accurate of the two operations without the other.

The relative rotation angle between a ray from the rotational center to the fiducial marker 13 and a ray from the rotational center to fiducial marker 24 is calculated by the using image processing in an image processing system 5 (shown in FIG. 4) to provide second angle information that serves as a measure of the relative rotation angle of the rotatable part 20 of the needle insertion guide device 1. Ideally, the second angle information would match the first angle information. However, due to noise in the images output by the X-ray CT scanner 3, and the resolution of the images output by the X-ray CT scanner 3, the measure of the relative rotation angle of the rotatable part 20 provided by the second angle information may not be exactly the same as the actual relative rotation angle of the rotatable part 20. Moreover, although the encoder sensor 12 is typically highly accurate, the encoder sensor 12 also has a finite resolution, and moreover it is possible that the encoder sensor 12 could experience a malfunction. Accordingly, the measure of the relative rotation angle of the rotatable part 20 provided by the first angle information may not be exactly the same as the actual relative rotation angle of the rotatable part 20. Frequently, one of the first angle information and the second angle information is more accurate than the other, and the more accurate of the two preferably is used to guide needle insertion, as discussed below.

Figure 5:
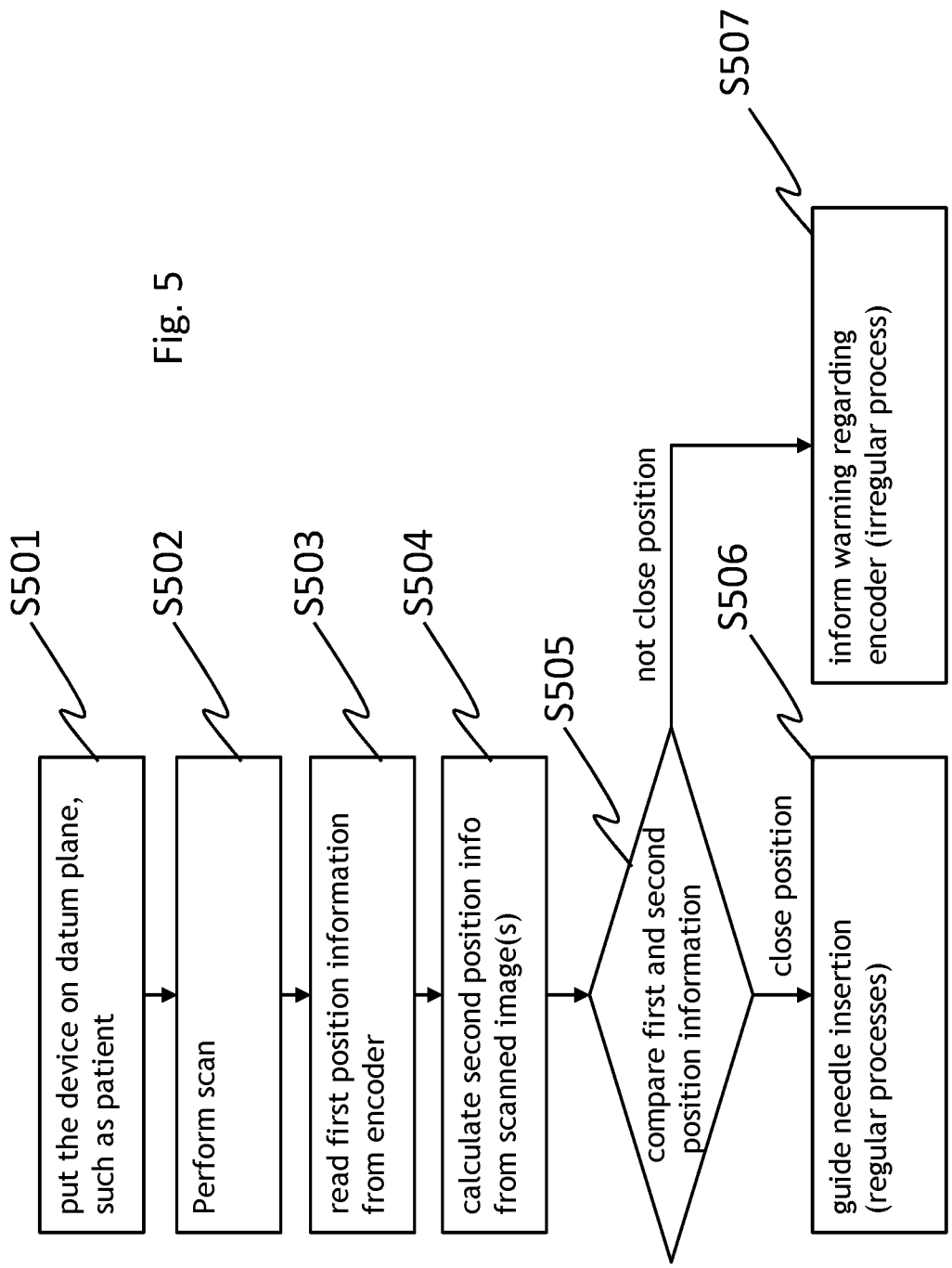
FIG. 5 is a flowchart of an example embodiment of a method of providing control guidance for the needle insertion guide device.

Referring now also to FIG. 5, there is shown a flowchart of an example embodiment of a method of providing control guidance for the needle insertion guide device 1. In step S501, the operator puts the needle insertion guide device 1 near a target portion one the patient while the patient is lying on a bed of the X-ray CT scanner 3. The operator can affix the needle insertion guide device 1 to the patient, for example by using sticky tape on the body of the patient if needed or desired. It is useful for the needle insertion guide device 1 be affixed so that the needle insertion guide device 1 does not slip down on a direction roughly along a tilt plane tangent to the body of the patient. Where operator should position the needle insertion guide device 1 on the patient can be determined, for example, by palpation, scout scan, or images scanned in the past, or medical knowledge of the operator.

After the needle insertion guide device 1 is put or fixed on the skin of the patient, in step S502 the X-ray CT scanner 3 scans patient body with the needle insertion guide device 1. During, or immediately before or after, scanning (discussed below), in step S503 the guidance system computer 2 reads the first angle information which the encoder 32 outputs.

In step S504, the guidance system computer 2 reads multiple two dimensional images and a reconstructed three dimension image of the patient from the X-ray CT scanner 3. The guidance system computer 2 detects positions of the fiducial markers 13, 23, 24, and 25 from the reconstructed three dimensional image using template matching algorithms and the fixed placement of those fiducial markers 23, 24, and 25 of the rotatable part 20 relative to one another. Alternatively, an operator may designate the positions of the fiducial markers 23, 24, and 25 instead of using such automatic registration. The guidance system computer 2 then calculates the second angle information with the positions of fiducial markers.

The following example process can be used for calculation of the second angle information. This example process transforms coordinates in a manner facilitates ease of understanding and may reduce computation. Represent a plane which includes all three of the fiducial markers 23, 24, and 25 by the X-Y plane of a three-dimensional Cartesian coordinate system with coordinates (X, Y, Z), with the Z direction specified from the X and Y directions in accordance with the right hand rule, (i.e., a right handed coordinate system). Represent the position where the rotational center of the encoder scale 22 intersects the X-Y plane by the position of the origin O=(0, 0, 0) of the three-dimensional Cartesian coordinate system. (Regarding notation, a point P=(x, y, z) can also be written P(x, y, z)). Represent an orthogonal direction with respect to the X-Y plane and through origin by the Z direction of the Cartesian coordinate system in accordance with the right-hand rule. Represent the distance from position of the fiducial marker 13 to the X-Y plane by h. Represent the position of the fiducial marker 13 by $P_{13}(x_0, y_0, -h)$. Represent the position of the fiducial marker 23 by $P_{23}(x_1, y_1, 0)$. Represent the position of the fiducial marker 24 by $P_{24}(x_2, y_2, 0)$. Represent the position of the fiducial marker 25 by $P_{25}(x_3, y_3, 0)$. Represent the projection along the Z-axis of the point $P_{13}$ onto X-Y plane by a point $Q(x_0, y_0, 0)$, with the direction from point O to point Q being the X direction, and with the coordinate $y_0$ being equal to 0.

Based on the above representations, the second angle information θ is a calculated value of the angle $\angle(Q, O, P_{24})$. The second angle information θ can be calculated by the following formulas because point O, $P_{24}$, and Q are on the above-noted X-Y plane, and the point Q is on X axis.

$$\theta = \text{atan2}(x_2, y_2), \text{ and} \qquad (1)$$

$$\text{atan2}(x, y) = \begin{cases} \arctan\dfrac{y}{x} & (x > 0) \\ \arctan\dfrac{y}{-x} + \pi & (x < 0, y \geq 0) \\ \arctan\dfrac{y}{-x} - \pi & (x < 0, y < 0) \\ 0 & (x = 0) \end{cases}.$$

Figure 3B:
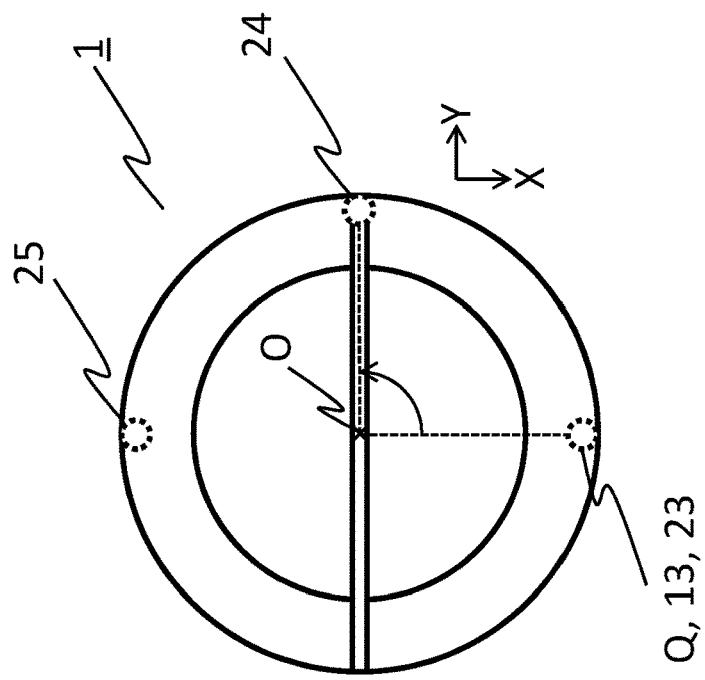
FIGS. 3A-3E are top views of the needle insertion guide device according to the first example embodiment.
Figure 3A:
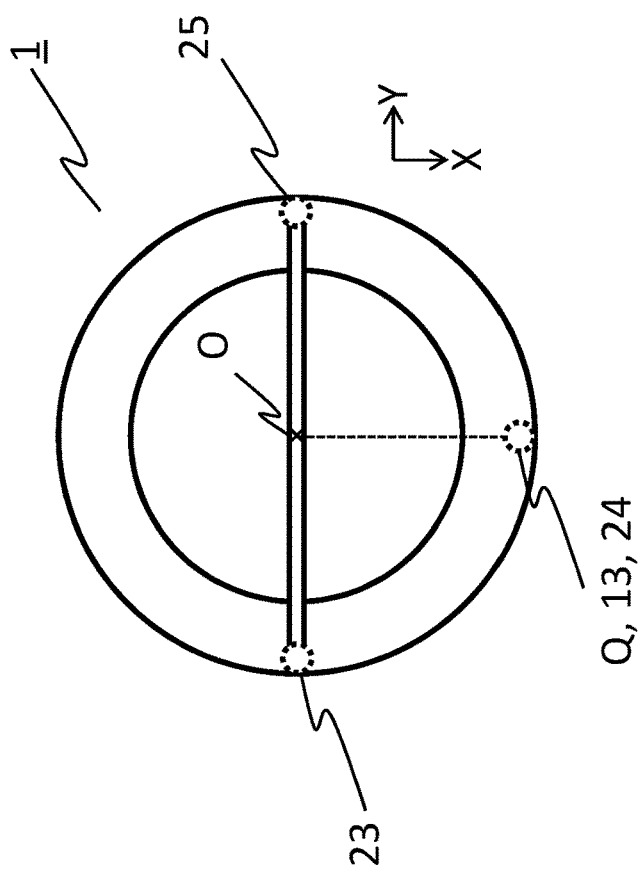
Figure 3D:
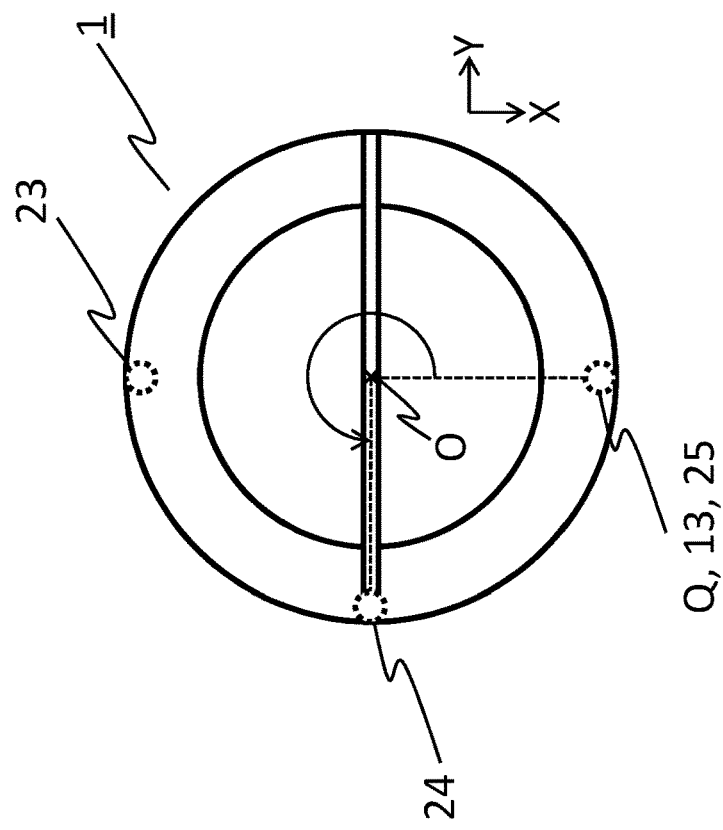
Figure 3C:
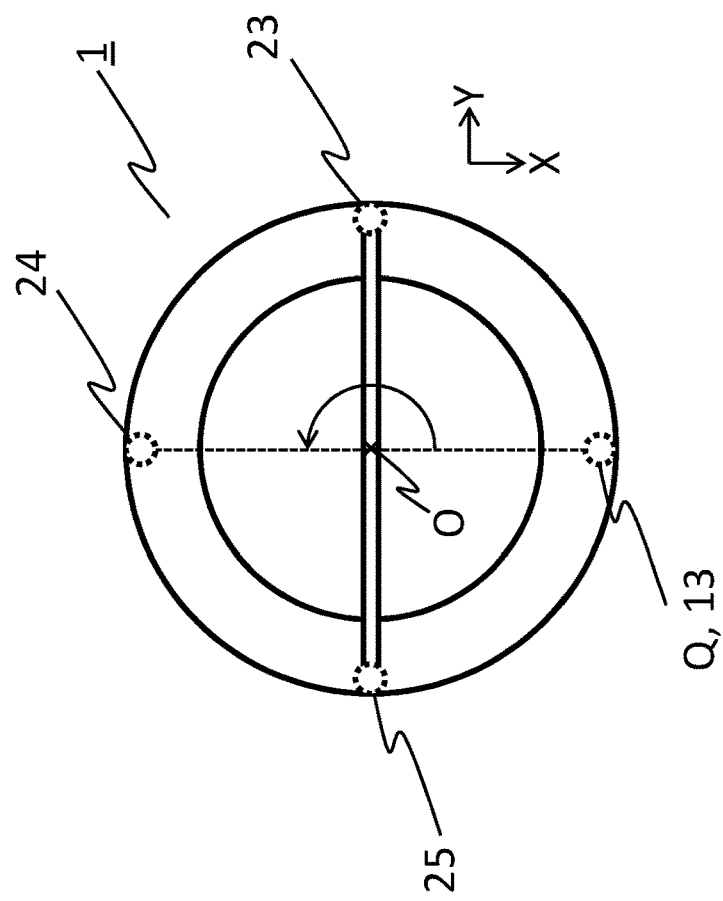

For example, when point $P_{24}$ overlaps point Q, the second angle information is 0 degrees, as shown in FIG. 3A. When point $P_{23}$ overlaps on point Q, the second angle information is 90 degrees, as shown in FIG. 3B. When point $P_{24}$ is directly opposite point Q with respect to the rotational axis (points Q and $P_{24}$ are opposite one another with respect to point O), the second angle information is 180 degrees, as shown in FIG. 3C. When point $P_{25}$ overlaps on point Q, the second angle information is 270 degrees, as shown in FIG. 3D.

Typically, if an encoder breaks, is irregular, or malfunctions, the encoder can detect the cause or causes of the breakage, irregularity, and/or malfunction and also output the status thereof. However, on rare occasions, an encoder outputs wrong position information without detecting a breakage, irregularity, or malfunction. By providing two operations to detect position information, the image processing and guidance system 5 can greatly reduce the probability of failure to recognize wrong position information as being wrong prior to application of medical treatment. In addition some of the causes of inappropriate or improper medical treatment are believed to be misalignments of instruments. By detecting position information both using the encoder 32 and using from images from the X-ray CT scanner 3, the image processing and guidance system 5 provides redundant detection of potential misalignments, and hence reduces the probability of misalignment yielding inappropriate or improper medical treatment.

To take advantage of the redundant detection, in step S505 the guidance system computer 2 compares the first angle information to the second angle information. Both first and second angle information may have some errors due to noise, distortion, mechanical tolerances, position errors, etc. Although they are not usually identical, the first angle information and the second angle information are usually close to one another in value unless the encoder 32 has broken. Accordingly, if in step S505 the first and second angle information are close enough (that is if in step S505 the first and second angle information are not different by a significant amount), then in step S506 the guidance system computer 2 informs the operator of the needle insertion angle and depth using the more accurate of the first angle information and second angle information, so that the operator or other medical staff can guide the needle to the target location. If the resolution of the X-ray CT scanner 3 is not fine, the first angle information is usually more accurate than the second angle information. However, if in step S505 the first and second angle information are not close enough (that is if in step S505 the first and second angle information are different by a significant amount), then in step S507 the guidance system computer 2 informs the operator to avoid a wrong guidance of the needle. For example, the guidance system computer 2 can guide the operator use the needle insertion guide device 1 to perform needle insertion based on the calculated value of the second angle information. Alternatively, the guidance system computer 2 can prompt the operator to replace the needle insertion guide device 1 and perform steps S501 through S505 again.

For example, to determine whether the first and second angle information are different by a significant amount, a threshold of difference can be set at a value more than the sum of worst case errors including mechanical error and position error. Mechanical error is caused by the slack of the needle insertion guide device 1 and can be estimated by tolerances. Position error which depends on the particular encoder used can be estimated by the specification of the encoder. Position error which depends on inaccurate determination of the positions of the fiducial markers 13, 23, 24, and 25 is caused by low resolution image reconstructed three-dimensional image of the patient from the X-ray CT scanner 3, which in turn can due to low resolution of the multiple two dimensional images provided by the scanning. Because a low resolution image cannot show the precise positions of the fiducial markers 13, 23, 24, and 25, the determined positions of fiducial markers 13, 23, 24, and 25 can have some amount of position error. The worst position error amount to be expected can be estimated by the resolution specification of the X-ray CT scanner 3. In this embodiment, the errors are specified as magnitudes (unsigned). In step S505, the guidance system computer 2 compares the first angle information to the second angle information as follows. First, the guidance system computer 2 determines the difference between the first angle information to the second angle information, for example, by subtracting one from the other, and then taking the absolute value of the result. If the difference between the first angle information and the second angle information is larger than sum of the above-noted errors, then at least one of the first angle information and the second angle information is incorrect. The threshold of difference can conveniently be set, for example, to twice of sum of the above-noted errors. If in step S505 the magnitude of the difference between the first angle information and the second angle information is larger than the threshold of difference, then in step S507 the guidance system computer 2 alerts the operator(s) by showing an error message on the display 4. In contrast, if in step S505 the magnitude of the difference between the first angle information and the second angle information is not larger than the threshold of difference, then in step S506 the guidance system computer 2 continues with providing guidance on needle insertion without first issuing the error message.

The present invention is not limited to use of the above-noted threshold of difference. For example, a practical threshold of difference can be calculated by combining a potential error magnitude of the second angle information and a potential error magnitude of the first angle information. A practical threshold of difference can be calculated by adding together (forming the sum of) the potential error magnitude of the second angle information and the potential error magnitude of the first angle information. Alternatively, if one of the potential error magnitudes is typically larger than the other(s), the larger can be doubled in value as an estimate of the combined effects of both. The potential error magnitude of the second angle information and the potential error magnitude of the first angle information can be estimated, for example, by processes discussed below.

Typically, quantization error of the scanning pitch is much larger than other forms of error. So the following process ignores errors that may affect the second angle information except for the quantization error. A fiducial marker can be visible on one or more images. When two or more images show the same fiducial marker, the position of that fiducial marker is set at a center position between the respective positions for that fiducial marker in the respective images. Whether one or more than one image show(s) the fiducial marker, the potential error magnitude of an individual fiducial marker is calculated as half of the scanning pitch. As more than one fiducial marker is used, the position as determined by image analysis may include such a displacement error due to quantization. Combination of displacement errors causes up to four times the error of the individual displacement error of a single fiducial marker (e.g., in radians). Thus, potential error magnitude of the second angle information in radians can be calculated as four times the individual displacement error of a single fiducial marker expressed in radians. If more than three fiducial markers are used, this same calculation formula can still be used, as using more fiducial markers usually increases accuracy. The error is roughly proportional to $(1/m)^{1/2}$, where m is the number of fiducial markers. Moreover, frequently the errors occur in the same direction for most or all of the fiducial markers, using the factor of four (4) in the above calculation provides a conservative estimate of the potential error magnitude of the second angle information. As the quantization error is generally much larger than other forms of error, a practical threshold of difference can be calculated as twice the estimate of the potential error magnitude of the second angle information.

As an example calculation of potential error magnitude of the second angle information, consider the following example device specifications. Provide each of the fiducial markers 13, 23, 24, and 25 with a spherical shape having a diameter of 10 mm. Provide the encoder 32 wherein the track of the encoder scale 22 is 25 mm, that is the portion of the encoder scale 22 tracked by the encoder sensor 12 has a central radius of 25 mm. Provide the X-ray CT scanner 3 with a scanning pitch on the Z direction of 5 mm, wherein the Z direction represents the direction that a bed of the X-ray CT scanner 3 moves to perform a scan. Further, provide the X-ray CT scanner 3 with a scanning resolution on X and Y directions of 0.5 mm. The potential error magnitude of an individual fiducial marker is 2.5 mm calculated as half of the scanning pitch 5 mm. Such a 2.5 mm error is equivalent to a 0.1 radian error on the circumference of the track of the encoder scale 22. Taking combinations of displacement into account, a conservative estimate of the potential error magnitude of the second angle information is 0.4 radians, and a practical threshold of the difference between the two angles can be calculated as u×0.4 radians. Applicable values for u are, for example, 1.5, 2, 2.5, or more, depending on the use. For example, when u=2, this gives a practical threshold of the different of 0.8 radians.

However, the potential error magnitude of the first angle information can also be explicitly calculated. In general, most errors of rotary encoders are caused by eccentricity of the encoder sensor 12 and/or the encoder scale 22 relative to a circular shape centered on the axis of rotation. The error due to eccentricity can be calculated by the following formula.

$$\text{error} = \frac{\varepsilon}{r} \cdot \sin\theta + \alpha [\text{rad}], \quad (2)$$

where $\varepsilon$ is the eccentricity, r is the radius of a track of an encoder scale, $\theta$ is ideal angle without eccentricity, and $\alpha$ is a constant determined by a direction of the eccentricity. For example, if the eccentricity is equal to 100 micrometers, and the radius of the track of the encoder scale is 25 mm, then $\varepsilon/r$=0.004 [radians]. Accordingly, based also on the conservative estimate of the potential error magnitude of the second angle information being 0.4 radians, an alternative practical threshold of difference can be calculated as 0.4 radians+0.004 radians=0.4004 radians, or more simply as either of 0.40 radians or 0.41 radians. A precise calculation of the practical threshold difference is not necessary, as a slightly smaller value may typically result in a small increase in false positive determinations of error, whereas a slightly larger value may typically result in a small decrease in false positive determinations.

Some scanners take images with bed position information because the bed of the scanner moves during scanning. If the operator prepares for the following operations before scanning, this embodiment can be implemented with just one fiducial marker on a movable part.

First, position a patient on a bed to place the needle insertion point at the designated position respect to a bed. Second, position the needle insertion guide device 1 on the body of the patient to align the index line 11 along the bed. Accordingly, the X direction and the position of the center of the needle insertion guide device 1 are known in scanned images. So, the guidance system computer 2 can detect the second angle information merely from the position of (point $P_{24}$ located at) the fiducial marker 24 (as in FIG. 3E).

As an alternative embodiment, note that the placements of fiducial markers are changeable because both the plane and the circle on at least three points are unique. Including more than three fiducial markers and/or including distinguishable fiducial markers provides further support to redundant detection of potential misalignments. Distinguishable fiducial markers can be provided, for example, using asymmetrical placement of fiducial markers, using fiducial markers which have a difference of absorptivity relative to one another, using fiducial markers which have a different shape or volume than one another. For example, in the reconstructed three-dimensional image of the patient from the X-ray CT scanner 3, a fiducial marker appears as a sectional shape of the respective three-dimensional shape of that fiducial marker. The sectional shape of a sphere is a circle, the sectional shape of a cube is a polygon, and the sectional shape of a cylinder is a circle, an ellipse, a rectangle, or other shape depending on the orientation of the cylinder. Accordingly, using fiducial markers of distinct respective three-dimensional shapes can yield distinct respective sectional appearances of the fiducial markers in the reconstructed three-dimensional image of the patient from the X-ray CT scanner 3.

As another alternative embodiment, the encoder 32 can be an incremental encoder instead of an absolute encoder. When an incremental encoder is used, the operator rotates the rotatable part 20 to detect index position.

As another alternative embodiment, the absorptivity of the encoder sensor 12 can be set to be different from the typical absorptivity of the body of a patient. Accordingly, the encoder sensor 12 will be visible in the scanned images from the X-ray CT scanner 3. The encoder sensor 12 can be thus made visible in the reconstructed three-dimensional image of the patient from the X-ray CT scanner 3, and the encoder sensor 12 thus can serve the role of a fiducial marker(s). For example, as the encoder sensor 12 is disposed on the fixed part 10, the encoder sensor 12, if made visible in the scanned images as noted above, can serve the role of the fiducial marker 13. In particular, a given portion of the encoder sensor 12 that is visible in the scanned images can serve the fiducial marker 13.

As another alternative embodiment, the encoder sensor 12 and the plurality of fiducial markers 23, 24, and 25 are disposed in the channel of rotatable part 20, and the encoder scale 22 and the fiducial marker 13 are disposed in the channel of fixed part 10. Furthermore, as a variation on this placement, if the encoder sensor 12 is visible in the scanned images, and is placed on the rotatable part 20, then the encoder sensor 12 can serve the role of one or more of the plurality of fiducial markers 23, 24, and 25, and thus the needle insertion guide device 1 can be implemented without the fiducial markers 23, 24, and 25.

Figure 3E:
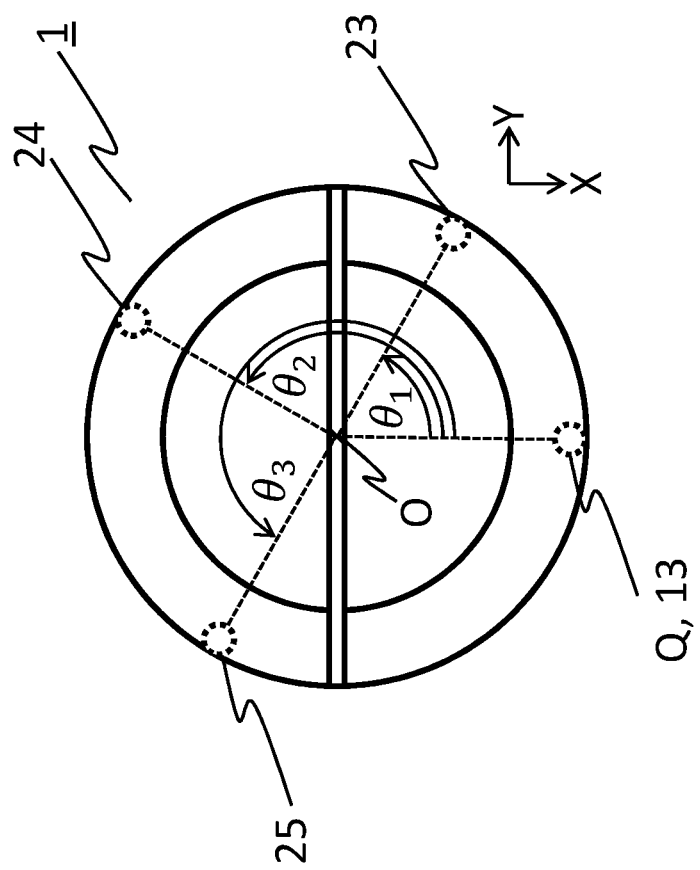

Referring now to FIG. 3E, there is shown an alternative implementation of the first example embodiment that can provide more accurate second angle information using an averaging processing. Although the second angle information is calculated as angle $\angle(Q, O, P_{24})$ in discussion provided above, the second angle information of this alternative implementation is provided by calculating an average value based on three angles $\theta_1=\angle(Q, O, P_{33})$, $\theta_2=\angle(Q, O, P_{24})$, and $\theta_3=\angle(Q, O, P_{25})$. Such an average can provide more accurate second angle information. Averaged second angle information θ can be calculated by the following formula. Because points $P_{23}$, $P_{24}$ and $P_{25}$ are placed on different angles, each of these angles is compensated in the following formula by a respective offset angle amount where i is an integer index which ranges over the number of angles used in the average. Thus, this formula also works with more than three fiducial markers, with appropriate respective offset angle amounts being specified.

$$\theta = \mod\left(\sum_{i=1}^{n} \frac{AntiAliasing(\theta_i - b_i, t)}{n}, 360\right) \text{[degrees], wherein} \quad (3)$$

$$AntiAliasing(x, t) = \begin{cases} \mod(x, 360) & (t-180 \le \mod(x, 360) < t+180) \\ \mod(x, 360) + 360 & (\mod(x, 360) < t-180) \\ \mod(x, 360) - 360 & (t+180 \le \mod(x, 360)) \end{cases}$$

[all in degrees], and wherein $n = 3$, $b_1 = 270$[degrees], $b_2 = 0$[degrees], $b_3 = 90$[degrees], $\mod(x, y)$ is the reminder of $\frac{x}{y}$, $t$ is an arbitrary value but near $\theta$ and $0 \le t < 360$[degrees], $n$ is the number of angles, and $b_i$ is the offset angle.

In the above averaging processing, offset angles $b_i$ are used in the calculation of the second angle information, and the processing works even with alternative placements of fiducial markers 23, 24, and 25 provided that appropriate offset angle values are specified. As another alternative, in implementations where the fiducial marker 25 leads the fiducial marker 24 by the same radian magnitude that the fiducial marker 23 lags the fiducial marker 24, an averaged second angle information θ can be calculated by the following alternative formula, $\theta=\frac{1}{3}(\theta_1+\theta_2+\theta_3)$, wherein offset values are not used because the above-noted lag and lead are equal in radian magnitude and hence essentially cancel each other out due to the averaging.

Another manner of implementing the needle insertion guide device 1 is to detect the center position by circle fitting. This can be beneficial, for example, because the difference between a detected center position and the real center position may cause some error(s) in calculated values. There are many algorithms that can be used to implement circle fitting. The following reference [1] may be helpful for guidance on various alternatives for implementing circle fitting. [1] I. D. Coope, Circle fitting by linear and nonlinear least squares, Journal of Optimization Theory and Applications, February 1993, Vol. 76, Issue 2, pp 381-388.

Referring now to FIG. 12, there is shown a sectional view of another alternative embodiment of the needle insertion guide device 1 in accordance with an example embodiment. In this embodiment, the needle insertion guide device 1 includes a magnetic encoder 432 instead of an optical encoder. The magnetic encoder 432 includes an encoder sensor 412 and an encoder scale 422. In this embodiment, the encoder sensor 412 is disposed in channel of the fixed part 10, and the encoder scale 422 is disposed in the channel of the rotatable part 20. The encoder scale carries information magnetically encoded along the circular path of the encoder scale 422. The encoder sensor 412 reads the magnetic information to the rotation angle of the rotatable part 20 relative to the fixed part 10. Although the principles of operation of a magnetic encoder are different from those of an optical encoder, from the standpoint of encoder output either type (optical or magnetic) of encoder can be used. Typically optical encoders provide a finer resolution of measure of angle than magnetic encoders, whereas magnetic encoders typically are more reliable than optical encoders (e.g., typically a higher mean time to failure).

Figure 6:
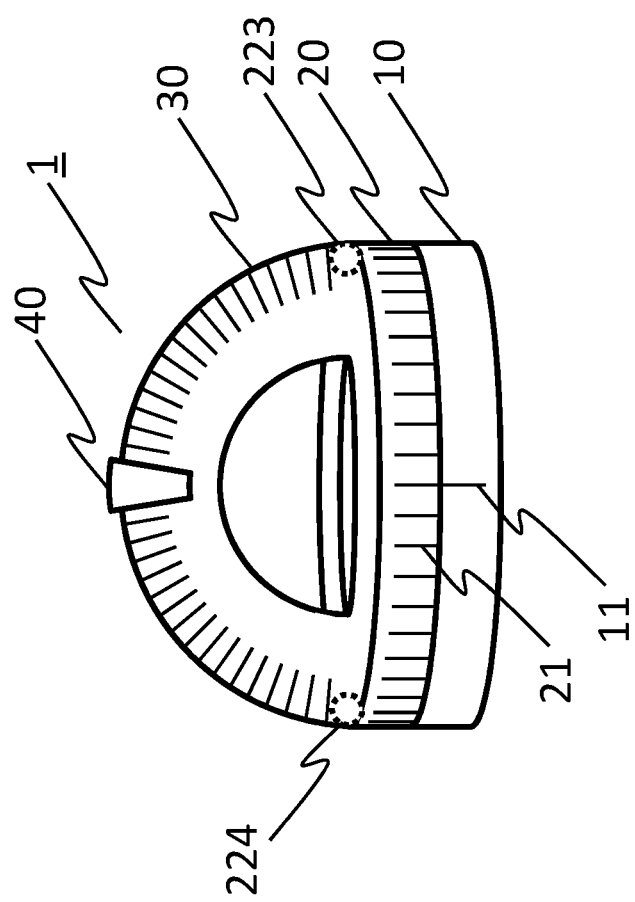
FIG. 6 is a perspective view of the needle insertion guide device that includes a handle according to an alternative example embodiment.

Referring now to FIG. 6, there is shown a perspective view of another alternative example embodiment of the needle insertion guide device 1. In this example embodiment, needle insertion guide device 1 includes a handle 30. The handle 30 is shaped as an arc, with two end portions of the arc affixed to or formed into a top surface of the rotatable part 20 and lying on opposite sides of the axis of rotation of the rotatable part 20, and with a top of the arc of the handle 30 disposed on the axis of rotation of the rotatable part 20. However, the handle 30 can alternatively be disposed away from the axis of rotation of the rotatable part 20. The handle can also alternatively be disposed at an angle relative to the axis of rotation of the rotatable part 20. A needle holder 40 is attached on the handle 30 in this example embodiment. A hole is provided through the needle holder 40 so that a needle can be inserted through the needle holder. The arc of the handle 40 serves as a rail along which the needle holder 40 can ride. The needle holder 40 is thus movable along the top of the arc of the handle 30. At least a front surface of the needle holder 40 is clear or translucent so that the needle can be seen in the hole of the needle holder 40 when in use. The needle holder 40 supports and guides the needle to assist the operator at inserting the needle into the patient at an appropriate angle and to an appropriate depth. The surface of the handle 30 includes many lines, each disposed at a distinct angle to show the needle insertion angle, and the lines can be marked with text showing the angle of insertion to assist the operator. The hole through the needle holder 40 runs in line with (e.g. roughly parallel to) that line or two lines to which it is most immediately adjacent. When a needle is inserted in the needle holder 40, an operator can see through the needle holder 40 and see both the lines of the surface of the handle 30 and the needle, which facilitates the operator reading the angle of needle insertion.

To use the needle insertion guide device 1 with a medical probe, the diameter of the hole can be made sufficiently large to accommodate the diameter of the probe. Moreover, in such case, an additional clear or translucent sleeve can be inserted into hole for use with smaller diameter probe or needles. To use the needle insertion guide device 1 with a scalpel, the handle of the scalpel is shaped as a thin cylinder so that the handle of the scalpel can be inserted into through the hole, for example, from the bottom of the hole. Alternatively, the cylindrical handle of the scalpel can be inserted through the top of the hole through the needle holder 40, and thereafter, the blade of the scalpel can be mounted to the handle of the scalpel.

Figure 7:
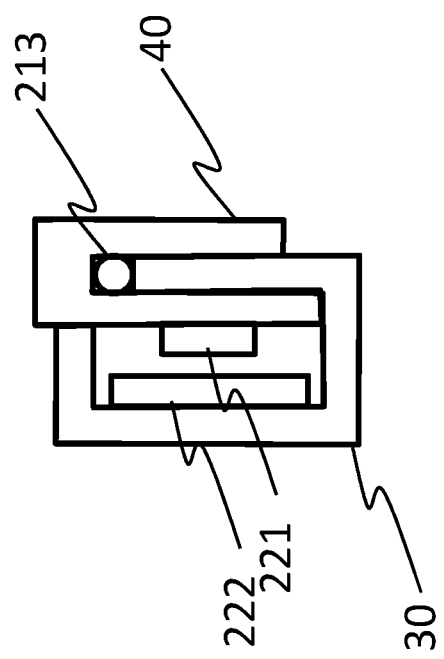
FIG. 7 is a sectional view of the handle of the needle insertion guide device in accordance with the alternative embodiment shown in FIG. 6.

In this example embodiment, an additional encoder 232 comprising an additional encoder scale 222 and an additional encoder sensor 221 are included. In particular, an encoder scale 222 and two fiducial markers 223 and 224 are disposed in the handle 30. An encoder sensor 221 and a fiducial marker 213 are affixed to a back surface of the needle holder 40. Referring now also to FIG. 7, there is shown a sectional view of the handle 30. The encoder scale 222 has the same or roughly the same arc shape as the handle 30. The encoder scale 222 and the encoder sensor 221 are disposed in opposition to one another, so the encoder sensor 221 faces and can read the encoder scale 222. When the needle holder 40 is moved along the top of the arc of the handle 30, for example to position the needle at an appropriate angle of insertion, the encoder sensor 221 moves along the encoder scale 222 and can read the encoder scale 222 to determine the insertion angle which would currently be provided by use of the needle holder 40. In this example embodiment, the encoder scale 222 is rigidly fixed to the handle 30, whereas the encoder sensor 221 is rigidly fixed to the needle holder 40 and thus movable along the encoder scale 222 and the arc of the handle 30. The encoder 232 shows the angle where needle holder 40 is currently located because an encoder sensor 221 moves with the needle holder 40. First angle information is the angle that the encoder provides as output. For ease of description, the encoder 232 in this example embodiment is assumed to be an absolute encoder. A relative encoder can alternatively be used. The encoder 232 is aligned to output additional first angle information. The first angle information output by encoder 232 is a measure of the needle insertion angle along the arc of the handle 30. Fiducial markers 223 and 224 are disposed on opposite ends of the handle 30 symmetrically. The central position between the fiducial markers 223 and 224 would be just above the skin of the patient when the needle insertion guide device 1 is in use. Accordingly, for purposes of analyzing output the X-ray CT scanner 3 to determine or specify a needle insertion angle on the arc of the handle 30, the needle insertion point and the three fiducial markers 213, 223 and 224 appear to lie on the same plane, in particular, a plane tangent to the skin of the patient at the needle insertion point. The guidance system computer 2 detects positions of the fiducial markers 213, 223, and 224 from the reconstructed three dimensional image using template matching algorithms and using the fixed placement of the fiducial markers 223 and 224 on opposite ends of the arc of the handle 30 relative to one another. Alternative, an operator may designate the positions of the fiducial markers 223 and 224 instead of using such automatic registration. The guidance system computer 2 then calculates additional second angle information using detected the positions of the three fiducial markers 213, 223 and 224.

Figure 8:
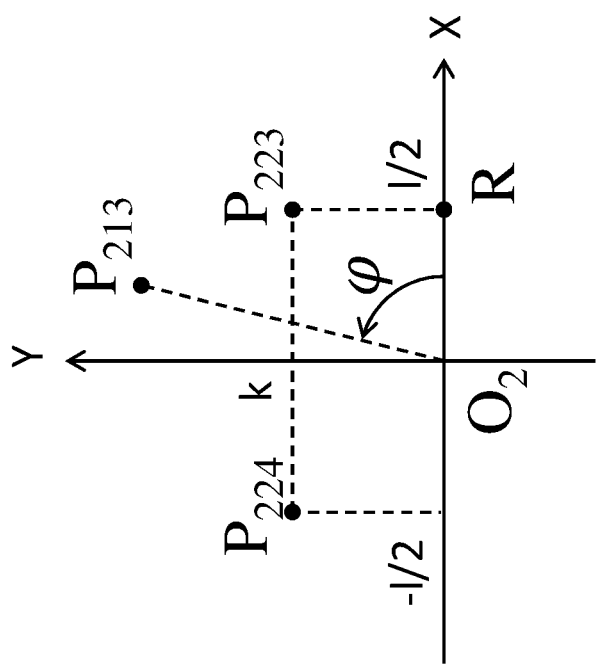
FIG. 8 is a diagram illustrating aspects of calculation of additional angle information $\varphi$ in accordance with the alternative embodiment shown in FIGS. 6 and 7.

The second angle information can be calculated by the following example process. This process transforms coordinates in a manner that is relatively easy to explain and that reduces calculation processing. Represent the distance between the fiducial markers 223 and 224 by l. Represent the height between the needle insertion point and the fiducial marker 223 or 224 by k. Represent a plane that includes the needle insertion point and that fiducial markers 223 and 224 are equidistant from an X-Y plane of a second Cartesian coordinate system with coordinates (X, Y). Note that this is a different Cartesian coordinate system (X, Y) than the first two coordinates of the Cartesian coordinate system (X, Y, Z) discussed above. Represent the needle insertion point by the position of the origin $O_2=(0, 0)$ of the second Cartesian coordinate system (X, Y). Represent the position of the fiducial marker 213 by $P_{213}(x_{213}, y_{213})$. Represent the position of the fiducial marker 223 by $P_{223}(l/2, k)$. Represent the position of the fiducial marker 224 by $P_{224}(-l/2, k)$. Represent the ray that lies in the X-Y plane and that is parallel to the ray from point $P_{224}$ to $P_{223}$ by the X direction of the second Cartesian coordinate system. Represent a ray in the X-Y plane that is orthogonal to X direction by the Y direction of the X-Y plane. Represent the point at coordinates (l/2, o) in the X-Y plane by R. The guidance system computer 2 calculates the additional second angle information $\varphi$ as being the angle $\angle(R, O_2, P_{213})$, as shown in FIG. 8. In this example embodiment, the additional second angle information $\varphi$ is calculated by the using the formula shown below, wherein $x_{213}$ and $y_{213}$ are determined by analysis of the three dimensional image reconstructed from scanned multiple two dimensional images output by the X-ray CT scanner 3.

$$\varphi = a\tan 2(x_{213}, y_{213}). \tag{4}$$

The needle insertion guide device 1 in accordance with the example embodiment shown in FIG. 6 includes two encoders 32 and 232. Alternatively, a handle 30 can be included without the encoder 232, or without the three fiducial markers 213, 223, and 224, or without both the encoder 232 and the three fiducial markers 213, 223, and 224. This may provide less guidance to the operator, but it is also less expensive to produce and may be adequate in some medical applications. As another alternative, the handle 30 can be included with the encoder 232 and/or the three fiducial markers 213, 223 and 224, but without the encoder 32 and/or the fiducial markers 13, 23, 24, and 25. This is also less expensive to produce and may be adequate in some medical applications.

Figure 9:
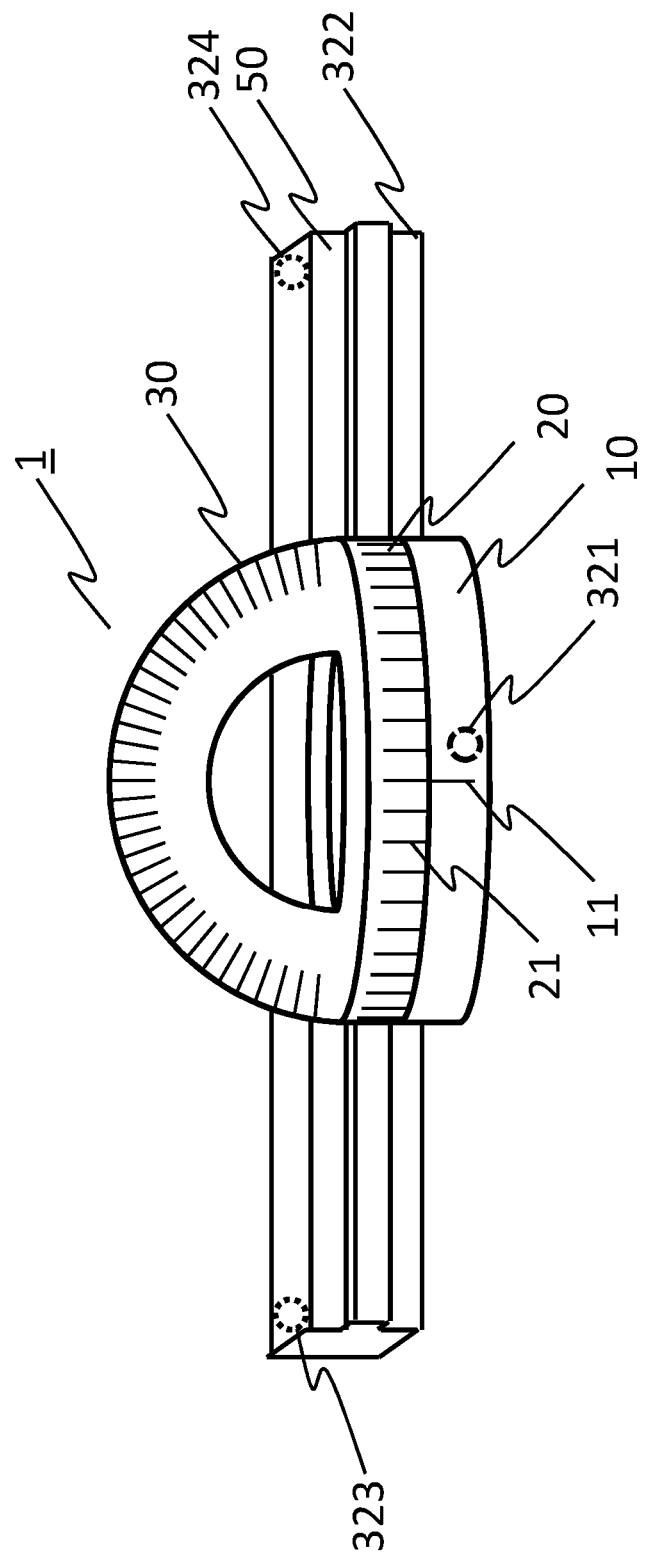
FIG. 9 is a perspective view of the needle insertion guide device that includes a linear encoder according to another example embodiment.
Figure 10:
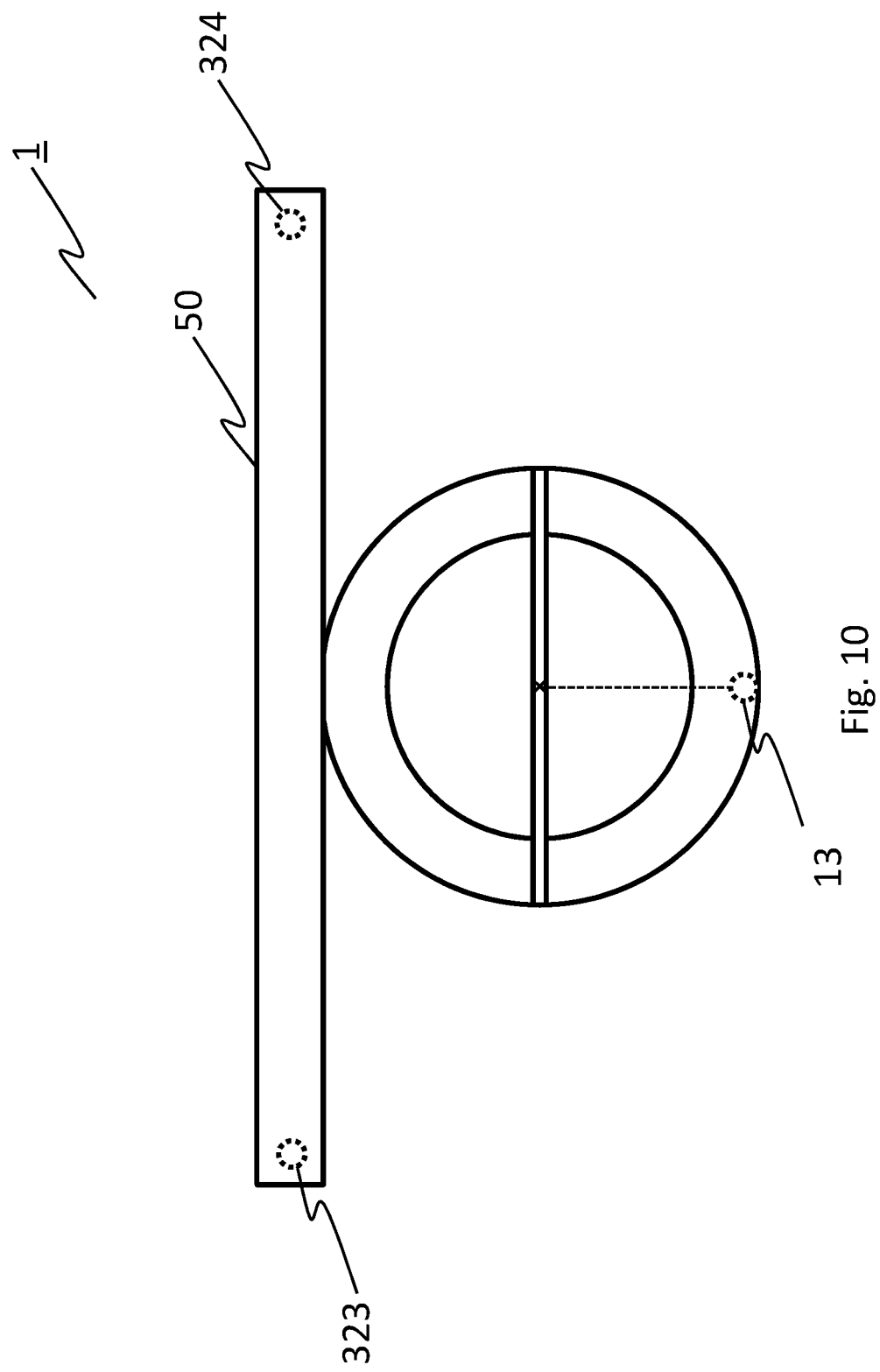
FIG. 10 is a top view of the needle insertion guide device with a linear guide in accordance with the example embodiment shown in FIG. 9.

Referring now to FIG. 9, there is shown a perspective view of another example embodiment of the needle insertion guide device 1 that further includes a linear encoder 332 having an encoder sensor 321 and a linear encoder scale 322. In this example embodiment, the linear guide 50 is placed above a bed of the X-ray CT scanner 3 so that the position of the axis of rotation of the rotatable part 20 can be adjusted along (e.g. tangent to) the skin of the patient. The needle insertion guide device 1 is attached to a linear guide 50 and is movable along the linear guide 50. A line 11 of the needle insertion guide device 1 faces outside and in an orthogonal direction relative to the movable direction. Although the bed of the X-ray CT scanner 3 is also movable, the needle insertion guide device 1 and the bed move independently. And also, the needle insertion guide device 1 does need to move during scanning, whereas the bed of the X-ray CT scanner 3 may move during scanning to support the scanning operations. Referring now also to FIG. 10, there is shown a top view of the linear guide 50 of the needle insertion guide device 1 in accordance with the example embodiment shown in FIG. 9. The linear guide 50 includes two fiducial markers 323 and 324 and the linear encoder scale 322. The two fiducial markers 323 and 324 are placed at opposite ends of the linear guide 50. Let the distance between the fiducial markers 323 and 324 be represented by w. The encoder sensor 321 is embedded in the needle insertion guide device 1 and detects the relative position information between the needle insertion guide device 1 and the linear guide 50. First position information is read by an encoder. Second position information is calculated by the position of the fiducial markers 323 and 324 in one or more X-ray CT scan(s). The encoder in this example embodiment is an absolute encoder for ease of explanation, but a relative encoder can alternatively be used. The encoder is aligned to output first position information which is a measure of the relative position of the needle insertion guide device 1 on the linear guide 50.

In the example embodiment of FIGS. 9 and 10, second position information is calculated by following process. This example embodiment also calculates using a three dimensional image reconstructed from multiple two dimensional images. This process transforms coordinates in a manner that is relatively easy to explain and that reduces calculation processing. Represent a plane which includes the fiducial markers 13, 323, and 324 by an X-Y plane of a third Cartesian coordinate system with coordinates (X, Y). Note that this is a different Cartesian coordinate system (X, Y) system than the second coordinate system (X, Y) discussed above. Represent the position of the fiducial marker 323 by the position of the origin $O_3=(0, 0)$ of the third Cartesian coordinate system (X, Y). Represent the position of the fiducial marker 324 by $P_{324}(x_{324}, 0)$. Represent the position of the fiducial marker 13 by $P_{13}(x_{13}, y_{13})$. Represent the point that is the perpendicular projection of $P_{13}$ to the line from $O_3$ to $P_{324}$ by $S(x_{13}, 0)$. Represent the ray from point $O_3$ to point S represent by the X direction. Represent a ray in the X-Y plane that is orthogonal to X direction by the Y direction.

Figure 11:
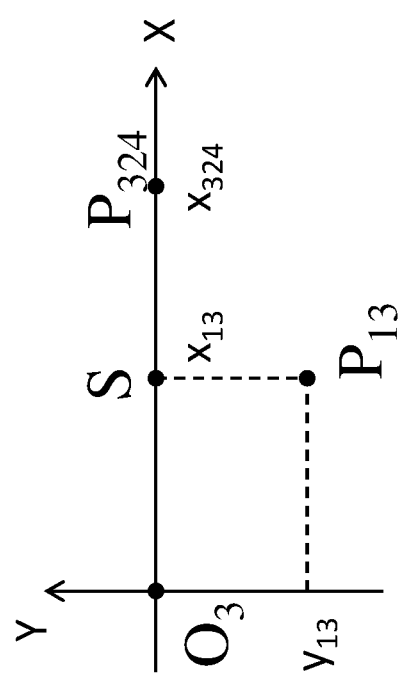
FIG. 11 is a diagram illustrating aspects of a relative positioning of device components in accordance with the example embodiment shown in FIGS. 9 and 10.

Referring now also to FIG. 11, there is shown a relative positioning of device components on the X-Y plane in accordance with the example embodiment of FIGS. 9 and 10. Because the distance between point $O_3$ and $P_{324}$ is represented by w, the second position information d can be calculated by the following formula.

$$d = \frac{x_{13}}{x_{324}} \cdot w. \quad (5)$$

Various embodiment(s) of the present invention, such as an image processing and guidance system for a needle insertion guide device, can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to example embodiments, it is to be understood that the invention is not limited to the disclosed example embodiments. The scope of the following claims is to be accorded the broadest interpretation so as to encompass all such modifications and equivalent structures and functions.

What is claimed is:

1. A medical tool insertion guide device comprising:
a base portion composed primarily of material transmissive of at least one band of electromagnetic radiation and having a first component composed of material absorptive of the at least one band of electromagnetic radiation, the base portion having a first mounting surface;
a movable portion composed primarily of material transmissive of the at least one band of electromagnetic radiation and having a second component composed of material absorptive of the at least one band of electromagnetic radiation, the movable portion configured to be mounted to the base portion and when so mounted movable relative to the base portion, the movable portion having a second mounting surface that faces the first mounting surface;
an encoder having an encoder sensor and an encoder scale, one of the encoder sensor and the encoder scale mounted to the first mounting surface, and another of the encoder sensor and the encoder scale mounted to the second mounting surface, the encoder sensor facing the encoder scale when the movable portion is mounted to the base portion.

2. The medical tool insertion guide device according to claim 1, wherein at least one of the base portion and the movable portion is composed primarily of plastic.

3. The medical tool insertion guide device according to claim 1, wherein at least one of the first component and the second component includes at least one fiducial marker.

4. The medical tool insertion guide device according to claim 1, wherein the at least one band of electromagnetic radiation includes an X-ray band.

5. The medical tool insertion guide device according to claim 1, wherein at least one of the first component and the second component includes at least one fiducial marker that is absorptive of X-ray radiation.

6. The medical tool insertion guide device according to claim 1, wherein the encoder sensor is absorptive of the at least one band of electromagnetic radiation serves as at least a portion of one of the first component and the second component.

7. The medical tool insertion guide device according to claim 1, wherein the encoder scale is absorptive of the at least one band of electromagnetic radiation and serves as at least a portion of one of the first component and the second component.

8. The medical tool insertion guide device according to claim 1, wherein the movable portion is rotably mounted to the base portion.

9. The medical tool insertion guide device according to claim 8, wherein the encoder sensor is configured to provide a first measure of a rotation angle of the rotatable portion relative to the base portion.

10. The medical tool insertion guide device according to claim 9, further comprising at least one programmable microprocessor programmed to provide a second measure of the rotation angle of the rotatable portion relative to the base portion by processing scan information of the medical tool insertion guide device provided by an electromagnetic radiation scanning device.

11. The medical tool insertion guide device according to claim 9, wherein the at least one programmable microprocessor is programmed to provide a second measure of the rotation angle of the rotatable portion relative to the base portion by processing scan information by an X-ray CT scanner.

12. The medical tool insertion guide device according to claim 8, further comprising at least one programmable microprocessor programmed to provide a second measure of the rotation angle of the rotatable portion relative to the base portion by processing scan information, of the medical tool insertion guide device and a patient, provided by an electromagnetic scanning device, and further programmed to compare the first measure to the second measure to determine a difference between the first measure and the second measure, and to provide a warning to an operator if the difference is greater than a threshold value.

13. The medical tool insertion guide device according to claim 8, further comprising at least one programmable microprocessor and a display unit, the at least one programmable microprocessor programmed to provide a second measure of the rotation angle of the rotatable portion relative to the base portion by processing scan information, of the medical tool insertion guide device and a patient, provided by an electromagnetic scanning device, and further programmed to determine which of the first measure and the second measure is a more accurate measure, and to display on the display unit an indication of which of the first measure to the second measure is the more accurate measure.

14. The medical tool insertion guide device according to claim 1, wherein the movable portion is rotably mounted to the base portion by a rotable mounting, and wherein at least one the first mounting surface and the second mounting surface includes at least an arc shaped portion, wherein a rotational center of the arc portion lies on an axis of rotation of the rotable mounting.

15. The medical tool insertion guide device according to claim 1, wherein the first mounting surface is disposed in a channel in the base portion, and wherein one of the encoder sensor and the encoder scale is mounted inside the channel and shielded by the channel from environmental conditions, the environmental conditions including at least one of ambient radiation and medical debris.

16. The medical tool insertion guide device according to claim 1, wherein the second mounting surface is disposed in a channel in the rotatable portion, and wherein one of the encoder sensor and the encoder scale is mounted inside the channel and shielded by the channel from environmental conditions, the environmental conditions including at least one of ambient radiation and medical debris.

17. The medical tool insertion guide device according to claim 1, wherein the encoder is an optical encoder.

18. The medical tool insertion guide device according to claim 1, wherein the encoder is a magnetic encoder.

19. The medical tool insertion guide device according to claim 1, wherein the encoder is an absolute encoder.

20. The medical tool insertion guide device according to claim 1, wherein the encoder is a relative encoder.

21. The medical tool insertion guide device according to claim 1, wherein base portion includes a first portion configured to be affixed to a patient, and a second portion mounted to the first portion and when so mounted movable in a linear direction along a surface of the first portion.

22. The medical tool insertion guide device according to claim 1, wherein the movable portion is rotably mounted to the base portion, and further comprising a linear guide portion,
wherein the linear guide portion is configured to be affixed to a patient, and the base portion is configured to be mounted to the linear guide portion to allow the base portion to be moved when so mounted in a linear direction along a surface of the linear guide portion.

23. The medical tool insertion guide device according to claim 1, wherein the movable portion is removable from the base portion and mountable to the base portion by an operator of the medical tool insertion guide device without usage of tools.

24. The medical tool insertion guide device according to claim 1, wherein the movable portion includes a protruding portion disposed away from the second mounting surface and accessible when the movable portion is mounted to the base portion.

25. The medical tool insertion guide device according to claim 24, wherein the protruding portion is acts as a handle for positioning the movable portion relative to the base portion.

26. The medical tool insertion guide device according to claim 24, wherein the protruding portion is acts as a handle for removing the movable portion from the base portion or for attaching the movable portion to the base portion.

27. The medical tool insertion guide device according to claim 24, wherein the protruding portion includes at least one fiducial marker and a medical tool holder, the medical tool holder mounted to the protruding portion and movable along the protruding portion, the medical tool holder configured to contact a portion of a medical tool to be guided by the medical tool insertion guide device, the medical tool holder including at least one fiducial marker, so that relative position of the medical tool holder along the protruding portion being is determinable by relative locations of the at least one fiducial marker of the protruding portion and the at least one fiducial marker of the medical tool holder in at least one scan image of the medical tool insertion guide device taken using electromagnetic radiation in the at least one band of electromagnetic radiation.

28. The medical tool insertion guide device according to claim 24, the medical tool being one of a needle, a medical probe, and a scalpel,
wherein the protruding portion includes a medical tool holder mounted to the protruding portion and movable along the protruding portion, and
wherein the medical tool holder includes a hole having a diameter sufficiently large to receive said one of the needle, the medical probe, and the scalpel, with the medical tool holder contacting and providing alignment support to the medical tool when so received.

29. A method of providing control guidance for a medical tool insertion guide device according to claim 1 using at least one scan of the medical tool insertion guide device by an electromagnetic radiation scan apparatus, the encoder provides a first measure of an alignment provided to a medical tool by the medical tool insertion guide device, the medical tool insertion guide device having at least one fiducial marker from which a second measure of the alignment provided to the medical tool by the medical tool insertion guide device is provided by computer processing of the at least one scan of the medical tool, the method comprising:
- comparing the first measure to the second measure by determining a difference between a value of the first measure and a value of the second measure; and
- determining whether the difference between the value of the first measure and the value of the second measure exceeds a predetermined threshold; and
- providing a warning to an operator of the medical tool insertion guide device that first measure may be inaccurate in response to the difference between the value of the first measure and the value of the second measure exceeding the predetermined threshold.

30. The method of providing control guidance for a medical tool insertion guide device according to claim 29, further comprising:
- calculating a first error magnitude estimate of the first measure based on at least one of a position error of the encoder and an amount of slack between portions of the medical tool insertion guide device;
- calculating a second error magnitude estimate of the second measure based on at least a quantization error component of resolution error of the at least one scan of the medical tool insertion guide device by an electromagnetic radiation scan apparatus;
- comparing the first error magnitude to the second error magnitude; and
- advising the operator, based on a result of the comparing, regarding which of the first measure and the second measure is more accurate.

31. A non-transitory computer-readable storage medium that stores a program of instructions that when executed by a computer cause the computer provide control guidance for a medical tool insertion guide device according to claim 1 using at least one scan of the medical tool insertion guide device by an electromagnetic radiation scan apparatus, the encoder provides a first measure of an alignment provided to a medical tool by the medical tool insertion guide device, the medical tool insertion guide device having at least one fiducial marker from which a second measure of the alignment provided to the medical tool by the medical tool insertion guide device is provided by computer processing of the at least one scan of the medical tool, the program of instructions comprising:
- instructions that when executed by the computer cause the computer to compare the first measure to the second measure by determining a difference between a value of the first measure and a value of the second measure; and
- instructions that when executed by the computer cause the computer to determine whether the difference between the value of the first measure and the value of the second measure exceeds a predetermined threshold; and
- instructions that when executed by the computer cause the computer to provide a warning to an operator of the medical tool insertion guide device that first measure may be inaccurate in response to the difference between the value of the first measure and the value of the second measure exceeding the predetermined threshold.

32. The non-transitory computer-readable storage medium according to claim 31, the program of instructions further comprising:
- instructions that when executed by the computer cause the computer to calculate a first error magnitude estimate of the first measure based on at least one of a position error of the encoder and an amount of slack between portions of the medical tool insertion guide device;
- instructions that when executed by the computer cause the computer to calculate a second error magnitude estimate of the second measure based on at least a quantization error component of resolution error of the at least one scan of the medical tool insertion guide device by an electromagnetic radiation scan apparatus;
- instructions that when executed by the computer cause the computer to compare the first error magnitude to the second error magnitude; and
- instructions that when executed by the computer cause the computer to advise the operator, based on a result of the comparing, regarding which of the first measure and the second measure is more accurate.

* * * * *